US010945684B2

(12) United States Patent
Tsubota et al.

(10) Patent No.: US 10,945,684 B2
(45) Date of Patent: Mar. 16, 2021

(54) ULTRASONIC CT DEVICE

(71) Applicant: Hitachi, Ltd., Tokyo (JP)

(72) Inventors: Yushi Tsubota, Tokyo (JP); Masakazu Sugaya, Tokyo (JP); Hideo Kashima, Tokyo (JP); Takahide Terada, Tokyo (JP); Kenichi Kawabata, Tokyo (JP); Wenjing Wu, Tokyo (JP); Kazuhiro Yamanaka, Tokyo (JP); Ai Masuda, Tokyo (JP)

(73) Assignee: HITACHI, LTD., Tokyo (JP)

( * ) Notice: Subject to any disclaimer, the term of this patent is extended or adjusted under 35 U.S.C. 154(b) by 117 days.

(21) Appl. No.: 16/272,583

(22) Filed: Feb. 11, 2019

(65) Prior Publication Data
US 2019/0290223 A1    Sep. 26, 2019

(30) Foreign Application Priority Data

Mar. 20, 2018  (JP) .............................. JP2018-052321

(51) Int. Cl.
*A61B 6/03*    (2006.01)
*A61B 8/13*    (2006.01)
*A61B 8/00*    (2006.01)
*A61B 8/14*    (2006.01)
*A61B 6/00*    (2006.01)
(Continued)

(52) U.S. Cl.
CPC ............ *A61B 6/032* (2013.01); *A61B 6/5247* (2013.01); *A61B 8/13* (2013.01); *A61B 8/46* (2013.01); *A61B 8/0825* (2013.01); *A61B 8/14* (2013.01); *A61B 8/15* (2013.01); *A61B 8/44* (2013.01); *A61B 8/4416* (2013.01); *A61B 8/463* (2013.01); *A61B 8/5261* (2013.01)

(58) Field of Classification Search
CPC ......... A61B 6/032; A61B 6/5247; A61B 8/13; A61B 8/4416; A61B 8/463; A61B 8/5261; A61B 8/4272; A61B 8/54; A61B 8/0825; A61B 8/15; A61B 8/44; A61B 8/46; A61B 8/14
See application file for complete search history.

(56) References Cited

U.S. PATENT DOCUMENTS 4,541,436 A * 9/1985 Hassler ................ A61B 8/0825
                                                              128/915
5,417,218 A    5/1995 Spivey et al.
(Continued)

FOREIGN PATENT DOCUMENTS

JP          8-508925 A    9/1996

*Primary Examiner* — Jon Chang
(74) *Attorney, Agent, or Firm* — Procopio, Cory, Hargreaves & Savitch LLP

(57) ABSTRACT

The ultrasonic CT device includes: a first water tank configured such that an object is inserted therein, the first water tank being filled with a medium through which an ultrasonic wave passes; a ring array that irradiates an ultrasonic wave to the object and detects an ultrasonic wave reflected by the object while moving on an outer surface of the first water tank; and a signal processing unit that generates a tomographic image of the object based on a signal obtained by the ring array. The ultrasonic CT device further includes: a second water tank that houses the first water tank and the ring array; and a lid having a hole or a notch which is provided on a side of the object in the second water tank and which drains the medium.

13 Claims, 8 Drawing Sheets

(51) Int. Cl.
  *A61B 8/08*  (2006.01)
  *A61B 8/15*  (2006.01)

(56) References Cited

U.S. PATENT DOCUMENTS

| | | | |
|---|---|---|---|
| 6,409,668 B1* | 6/2002 | Wollschlaeger | A61B 8/0825 600/443 |
| 2004/0064046 A1* | 4/2004 | Shehada | A61B 8/406 600/437 |
| 2005/0143638 A1* | 6/2005 | Johnson | A61B 5/415 600/407 |

* cited by examiner

[FIG. 2]
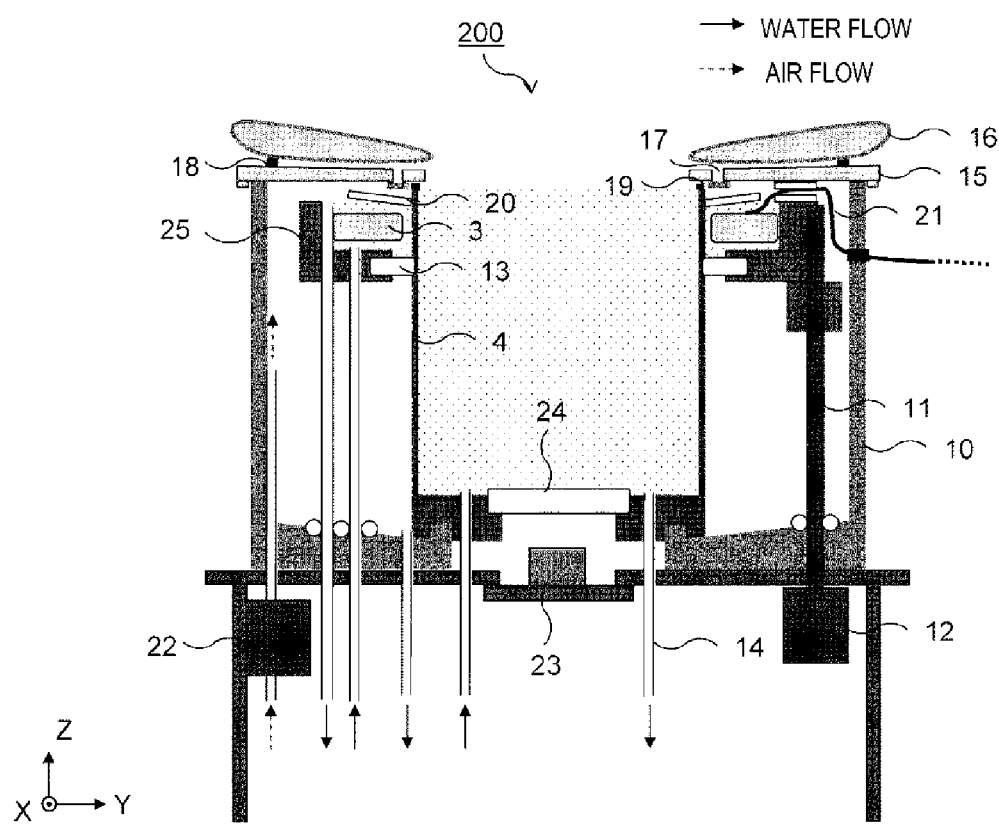

[FIG. 4]
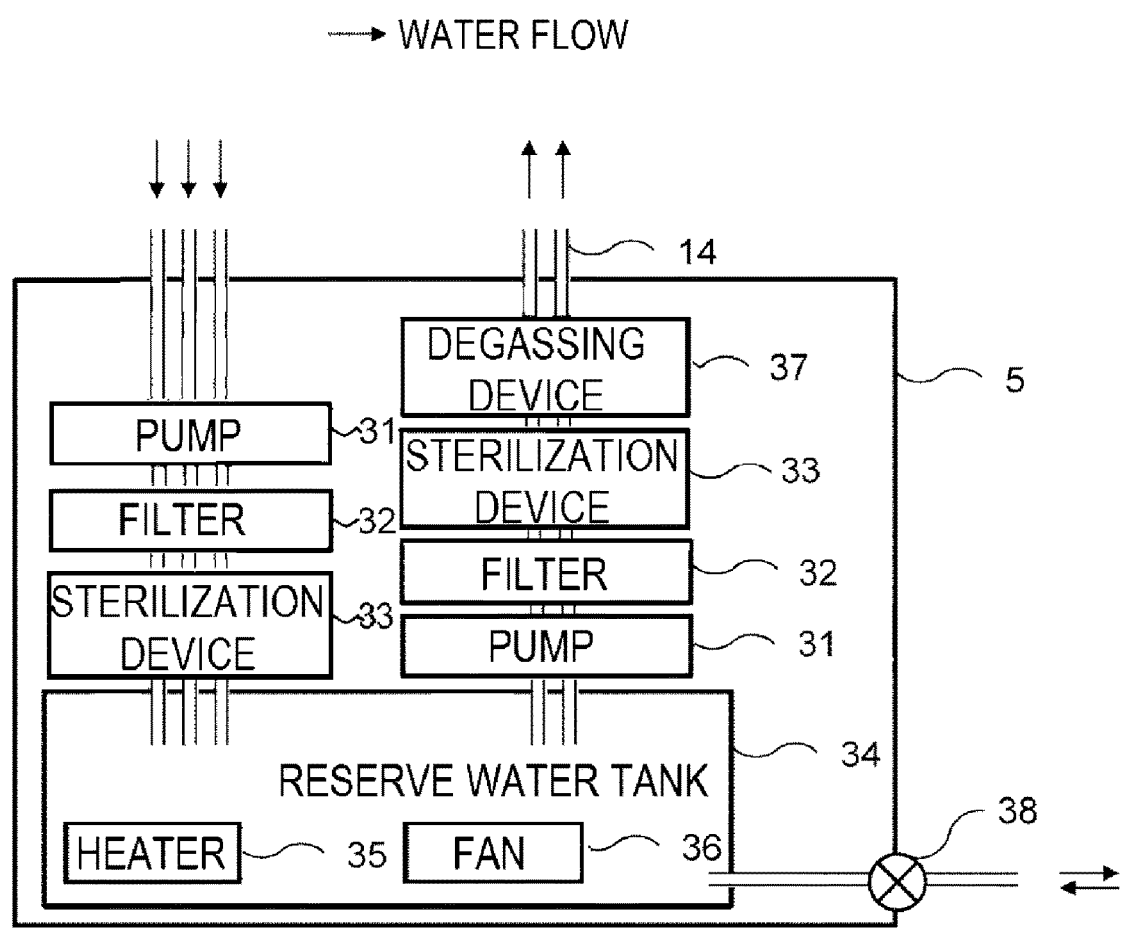

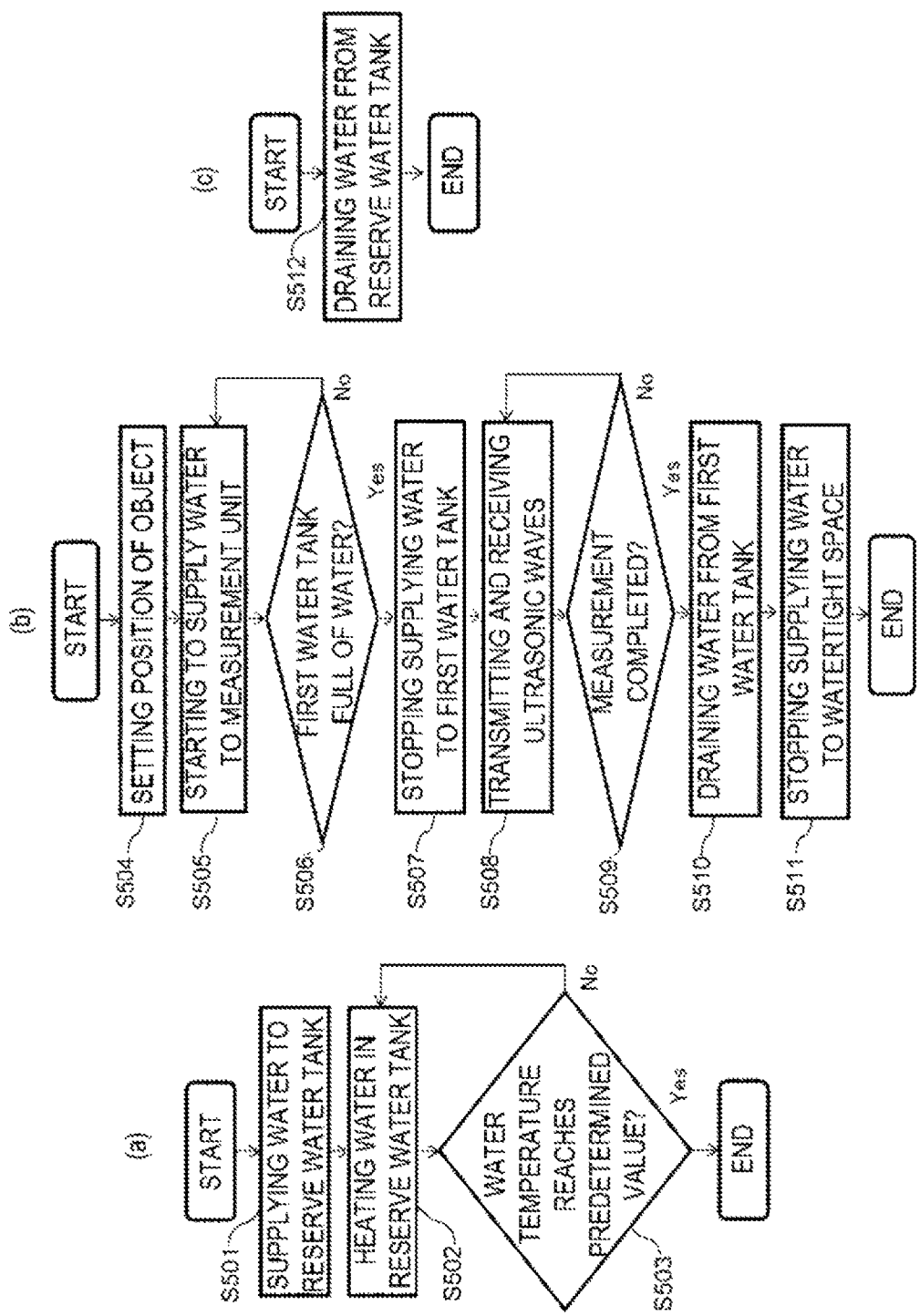

[FIG. 7]
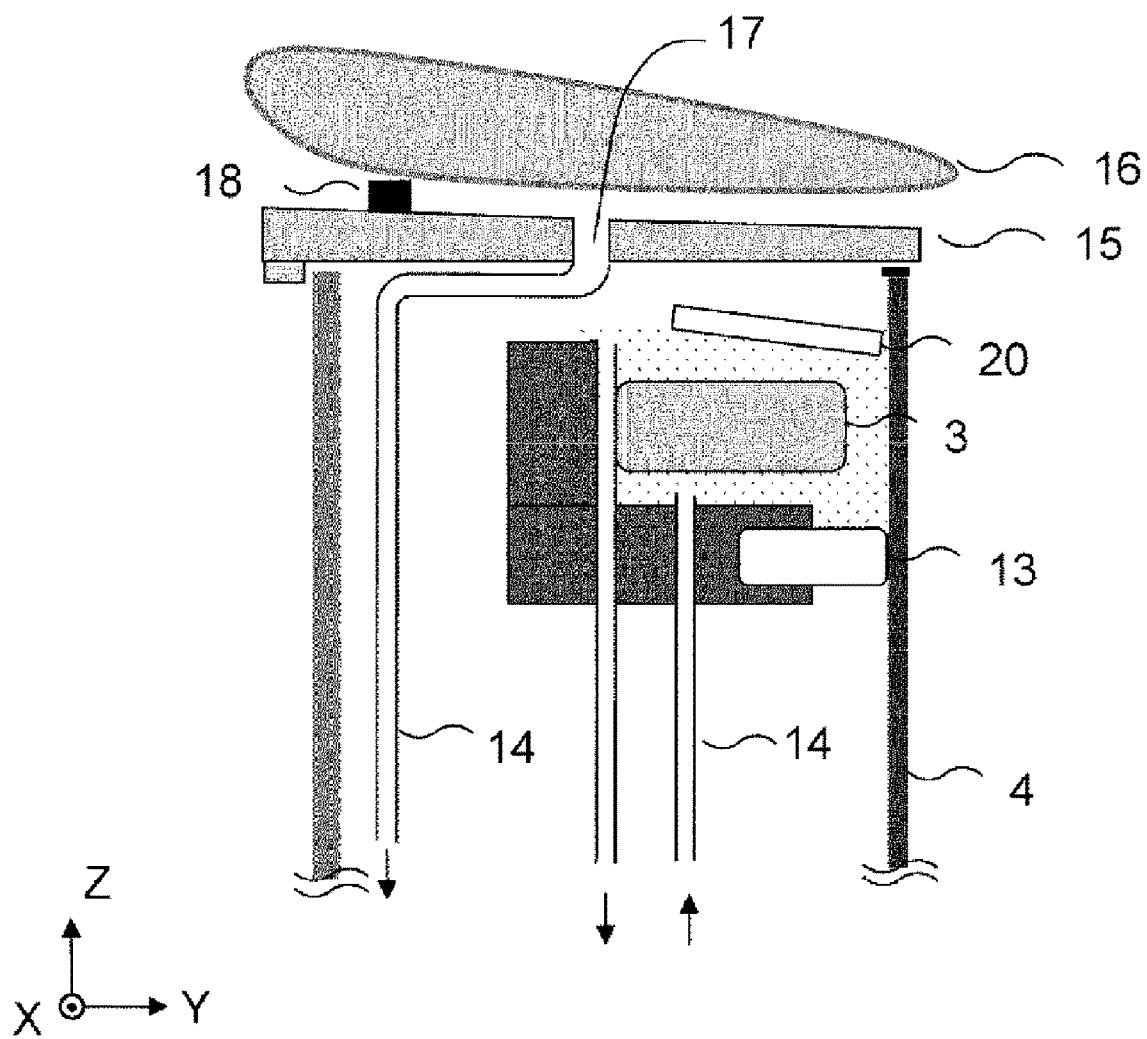

ULTRASONIC CT DEVICE

CLAIM OF PRIORITY

The present application claims priority from Japanese Patent Application JP 2018-052321 filed on Mar. 20, 2018, the content of which are hereby incorporated by references into this application.

TECHNICAL FIELD

The present invention relates to an ultrasonic CT device, and to a water tank into which an object is inserted.

BACKGROUND ART

An ultrasonic CT (Computerized Tomography) device is a device that irradiates an object with ultrasonic waves from a plurality of directions and makes a tomographic image of a physical property in the object, such as a sound speed or an attenuation coefficient of ultrasonic waves, from a signal obtained by detecting ultrasonic waves that pass through the object. In irradiation and detection of the ultrasonic waves, a ring array in which piezoelectric elements are arranged in a circular ring shape is used, and the signal is obtained in a state where the object is inserted into the ring array. In order to prevent attenuation of the obtained signal, a medium through which ultrasonic waves easily pass, such as warm water, is filled between the ring array and the object.

PTL 1 discloses an ultrasonic CT device in which a ring array is movable in a vertical direction in an oil tank, the oil tank surrounding a cylindrical-shaped water tank, a breast serving as an object being inserted into the cylindrical-shaped water tank. Since an imaging field in the vertical direction of the ultrasonic CT device depends on a quantity of a medium in the water tank, the water tank is filled with the medium in order to ensure a wide imaging field in the vertical direction.

PRIOR ART LITERATURE

Patent Literature

PTL 1: JP-T-08-508925

SUMMARY OF INVENTION

Technical Problem

However, in PTL 1, no attention is paid to an influence of the medium that overflows from the water tank due to body movement of the object on a periphery of the water tank. When the medium overflowing from the water tank flows to an unexpected place, for example, an electronic device, breakdown of the ultrasonic CT device may be caused due to a short circuit.

Therefore, an object of the invention is to provide an ultrasonic CT device that can reduce an influence of a medium overflowing from a water tank on a periphery of the water tank.

Solution to Problem

In order to achieve the above object, the invention provides an ultrasonic CT device including: a first water tank configured such that an object is inserted therein, the first water tank being filled with a medium through which an ultrasonic wave passes; a ring array configured to irradiate the object with an ultrasonic wave and to detect an ultrasonic wave reflected by the object while moving on an outer surface of the first water tank; and a signal processing unit configured to generate a tomographic image of the object based on a signal obtained by the ring array, the ultrasonic CT device further including: a second water tank configured to house the first water tank and the ring array; and a lid having a hole or a notch which is provided on a side of the object in the second water tank and is configured to drain the medium.

Further, the invention provides an ultrasonic CT device including: a first water tank configured such that an object is inserted therein, the first water tank being filled with a medium through which an ultrasonic wave passes; an ultrasonic element array arranged on an outer surface of the first water tank, the ultrasonic element array being configured to irradiate the object with an ultrasonic wave, and to detect an ultrasonic wave reflected by the object; and a signal processing unit configured to generate a tomographic image of the object based on a signal obtained by the ultrasonic element array, the ultrasonic CT device further including: a second water tank configured to house the first water tank and the ultrasonic element array; and a lid that is provided on a side of the object in the second water tank; in which a slit is provided in an uppermost portion of the first water tank.

Advantageous Effect

According to the invention, it is possible to provide an ultrasonic CT device that can reduce an influence of a medium overflowing from a water tank on a periphery of the water tank.

BRIEF DESCRIPTION OF DRAWINGS

FIG. 2 is a view showing a detailed structure of a measurement unit 200 according to a first embodiment.

FIG. 4 is a diagram illustrating a water adjustment unit 5.

FIG. 5 illustrates flowcharts showing an example of a processing flow related to water supply and drainage.

FIG. 7 is a view showing a structure of the measurement unit 200 according to a third embodiment.

DESCRIPTION OF EMBODIMENTS

It is desired that an ultrasonic CT device is used as a breast cancer examination device that can be applied to a relative young generation since, unlike X-ray mammography, the ultrasonic CT device has no radiation exposure. In the following description, although embodiments in which the invention is applied to a breast cancer examination device are described, an object is not limited to the breast.

First Embodiment

Figure 1A:
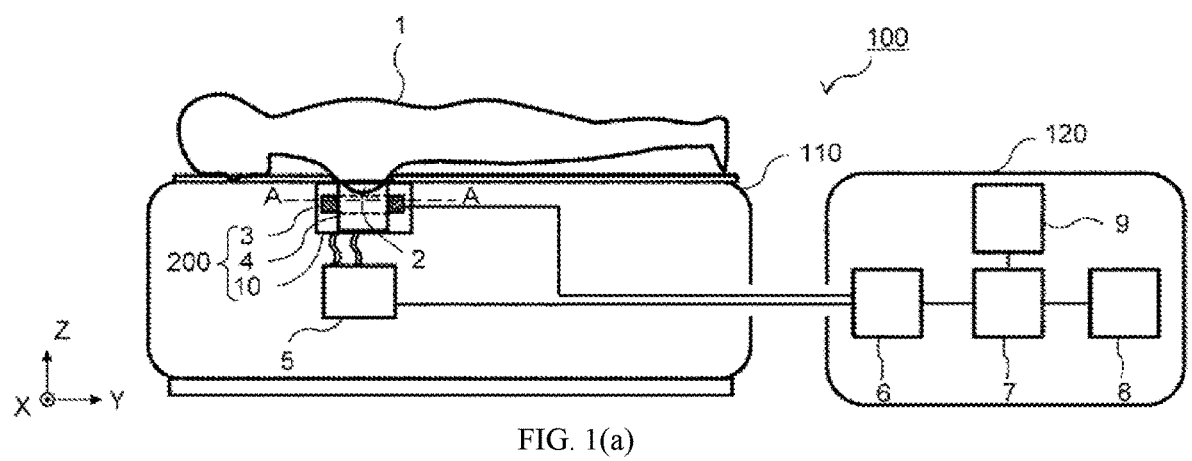
FIGS. 1(a) and 1(b) illustrate views illustrating an entire configuration of an ultrasonic CT device 100.
Figure 1B:
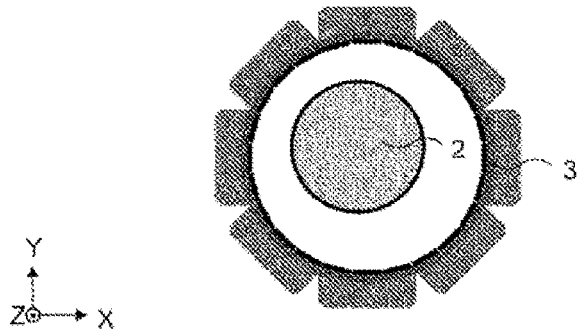

An entire configuration of an ultrasonic CT device 100 will be described with reference to FIG. 1. FIG. 1(a) is a sagittal cross-sectional view, and FIG. 1(b) is a cross-sectional view taken along a line A-A in FIG. 1(a). The ultrasonic CT device 100 includes a bed 110 and a console 120. A subject 1 in a prone position is placed on the bed 110. The bed 110 includes a measurement unit 200 that measures a breast serving as an object 2 and a water adjustment unit 5 that adjusts a water quantity and a water pressure inside the measurement unit 200.

The measurement unit 200 includes a first water tank 4, a ring array 3 and a second water tank 10. The first water tank 4 has a cylindrical shape, and is formed of a material through which an ultrasonic wave easily passes, for example, polyethylene. In the first water tank 4, the object 2 is inserted and a medium such as warm water is filled. The medium filling the first water tank 4 is supplied thereto after being heated, purified and degassed by the water adjustment unit 5.

The ring array 3 includes a plurality of ultrasonic elements such as piezoelectric elements disposed on an outer surface of the first water tank 4 in a circular ring shape. The ultrasonic elements, as shown in FIG. 1(b), may have a configuration in which several small portions arranged in a circular-arc shape are combined. The ultrasonic elements of the ring array 3 irradiate the object 2 with ultrasonic waves, and detect ultrasonic waves passing through the object 2 and ultrasonic waves reflected by the object 2. The ring array 3 moves in parallel on the outer surface of the first water tank 4 in a vertical direction (Z direction). The first water tank 4 and the ring array 3 are housed in the second water tank 10. A detailed structure of the measurement unit 200 will be described below with reference to FIG. 2.

The console 120 includes a control unit 6, a signal processing unit 7, a storage unit 8, and an input/output unit 9. The control unit 6 has various controllers those control the measurement unit 200 and the water adjustment unit 5. The controller for the measurement unit 200 controls transmission, reception and switch of an ultrasonic signal in the ring array 3, and movement of the ring array 3 in the vertical direction. The controller for the water adjustment unit 5 controls pressure, temperature, purification, and degassing or the like of the medium supplied by the water adjustment unit 5. These controls are performed based on control signals obtained by processing imaging conditions using a Central Processing Unit (CPU) of the signal processing unit 7 or the like, the imaging conditions being set by a user through a touch panel, a keyboard of the input/output unit 9 or the like. The set imaging conditions or the like are saved in a memory or a hard disk drive of the storage unit 8 or the like.

A signal obtained by the ring array 3 is recorded in the storage unit 8 and is used for image processing calculation in the signal processing unit 7. Tomographic images of the object 2 or the like generated by the image processing calculation are displayed on a monitor of the input/output unit 9 or the like. Further, the control unit 6, the signal processing unit 7 and the storage unit 8 may be housed in the bed 110. With such a structure, the tomographic images of the object 2 in the first water tank 4 are presented to a user, and image diagnostics are possible.

The detailed structure of the measurement unit 200 will be described with reference to FIG. 2. The ring array 3 is stored in a storage container 25, and the storage container 25 is connected to a ball screw shaft 11 so as to move in the vertical direction on the outer surface of the first water tank 4 by drive of a motor 12. As the storage container 25 moves, the ring array 3 moves in the vertical direction. In order to facilitate propagation of the ultrasonic wave, a space between the ring array 3 and the first water tank 4 is filled with a medium through which the ultrasonic wave passes, such as warm water or ultrasonic wave jelly. In order to prevent the medium from leaking from a space between the storage container 25 and the first water tank 4 even when the storage container 25 and the ring array 3 move in the vertical direction, a rubber member of the storage container 25 on the first water tank 4 side, which has low friction and high liquid tightness, is attached to contact the outer surface of the first water tank 4. A cover 20 that suppresses oscillation of a medium surface is attached above the ring array 3. A space surrounded by the storage container 25, the rubber member 13 and the cover 20 is called a watertight space. Similarly to the first water tank 4, the medium heated, purified and degassed from the water adjustment unit 5 is supplied to the watertight space through a tube 14. Further, in order to maintain a state suitable for measuring the medium in the watertight space and in the first water tank 4, the medium is circulated by returning to the water adjustment unit 5 through the tube 14.

The watertight space is housed in the second water tank such that even if the medium of the watertight space is leaked from a space between the storage container 25 and the cover 20, no trouble will be caused. A wall surface of the second water tank 10 may be made of an optically transparent material such that a state inside can be easily observed from outside. A lower portion of the second water tank 10 is inclined toward a water drainage port so as to have a structure suitable for drainage. A lid 15 having a circular opening into which the object 2 is inserted is attached to an upper portion of the second water tank 10. The lid 15 prevents a matter from falling into the second water tank 10, and prevents the ring array 3 from being damaged by falling of the matter. The lid 15 is inclined toward the first water tank 4 so as to have a structure suitable for returning the medium overflowing over the lid 15 to the first water tank 4. Further, the lid 15 includes a cushion member 16 in contact with the subject 1. The cushion member 16 has a circular opening into which the object 2 is inserted, and is inclined toward the opening. Waterproof treatment is performed on a surface of the cushion member 16.

Figure 3A:
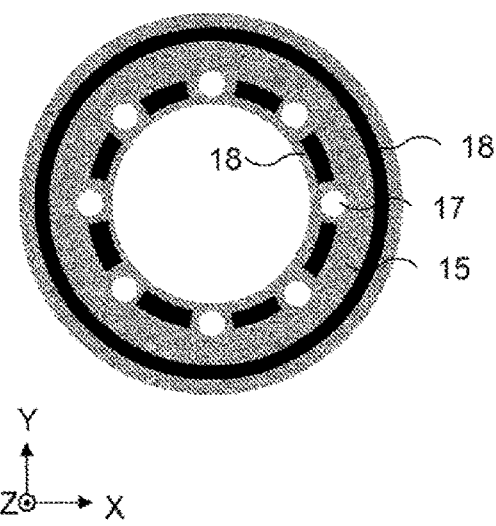
FIGS. 3(a) and 3(b) illustrate top views of a lid 15.
Figure 3B:
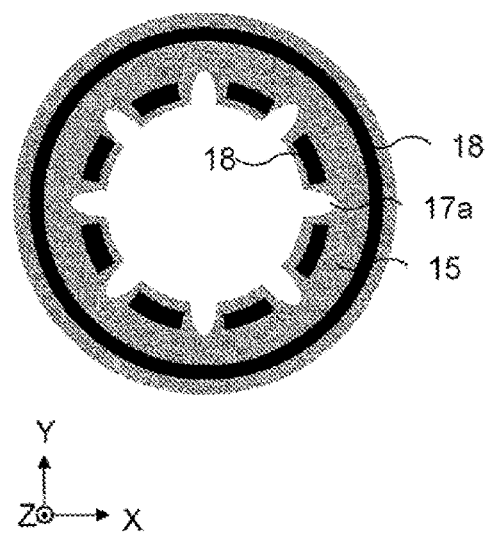

The lid 15 will be described with reference to FIG. 3 that illustrates top views of the lid 15. The lid 15 having holes 17 that drain the medium overflowing from the first water tank 4 to the second water tank 10 is shown in FIG. 3(a). A lid 15 having notches 17a that drain the medium overflowing from the first water tank 4 to the second water tank 10 is shown in FIG. 3(b). Even when a cushion member 16 is deformed by placing the subject 1 on the bed 110, holding members 18 made of rubber are disposed on the lid 15 so as to maintain a path for the medium to the holes 17 or the notches 17a. The holding members 18 are also disposed at an outer edge of the lid 15 and are adhered to the cushion member 16 such that the medium does not flow out to outside of the second water tank 10. It is desired that the lid 15, the holding members 18 and the cushion member 16 can be repeatedly detachable, so that the lid 15 and the cushion member 16 can be cleaned. Moreover, it is preferred that the holding members 18 are disposed such that cleaning can be easy.

Since the lid 15 has the holes 17 or the notches 17a, the medium overflowing from the first water tank 4 can be drained to the second water tank 10. Further, the holding members 18 are disposed on the lid 15. Accordingly, even when the cushion member 16 is deformed by placing the subject 1 on the bed 110, a water drainage capacity to the second water tank 10 can be maintained since the path of the medium is maintained.

The description returns to FIG. 2. In order to remove hair and dust, a thin filter 19 is adhered to the holes 17 of the lid 15. The thin filter 19 may be provided above the cover 20 or at an end portion of the tube 14. Since an ultrasonic control signal wire 21 connected to the ring array 3 may contact the medium, it is preferred that waterproof treatment is performed thereto. In order to control humidity inside the second water tank 10, warm air may be sent from a hairdryer 22 through the tube 14. Further, the warm air of the hairdryer 22 may be sent through the holes 17 to dry a body surface of the subject 1. A replaceable desiccant may be enclosed in the second water tank 10.

It is desired that a bottom surface of the first water tank 4 is formed of an optically transparent member 24. In a case where the bottom surface of the first water tank 4 is the optically transparent member 24, an optical camera 23 is attached to a lower portion of the first water tank 4, so that a position and a volume of the object 2 inside the first water tank 4 can be measured. Utilization of the measured position and volume of the object 2 will be described below.

The water adjustment unit 5 will be described with reference to FIG. 4. The medium, which is sent through the tube 14 from the measurement unit 200 to the water adjustment unit 5 by a pressure of a pump 31, is stored in a reserve water tank 34 through a filter 32 and a sterilization device 33. After being heated by a heater 35 and stirred by a fan 36, the medium of the reserve water tank is again through the filter 32, the sterilization device 33 and a degassing device 37 by the pressure of the pump 31, thereby being sent independently to the first water tank 4 and the second water tank 10 of the measurement unit 200. A plug 38 that is capable of directly supplying and draining water may be provided at the reserve water tank 34.

An example of a processing flow related to water supply and drainage is shown with reference to FIG. 5. FIG. 5(a) is a processing flow before measurement and during measurement preparation; FIG. 5(b) is a processing flow during the measurement; and FIG. 5(c) is a processing flow after the measurement. Hereinafter, each step will be described. First, FIG. 5(a) will be described.

(S501)

Water is stored in the reserve water tank 34. Water supply to the reserve water tank 34 is performed by operation of the plug 38 by a user, or by control of the plug 38 performed by the controller for the water adjustment unit 5 based on an instruction of the user.

(S502)

The water adjustment unit 5 heats the water inside the reserve water tank 34 by the heater 35 and stirs the water by the fan 36.

(S503)

The water adjustment unit 5 measures water temperature with a thermometer provided inside the reserve water tank 34. If the water temperature does not reach a predetermined value, the processing returns to S502; if the water temperature has reached the predetermined value, the preparation is completed and the processing proceeds to FIG. 5(b).

(S504)

The position of the object 2 is set. The subject 1 lies on the bed 110 with her face down and inserts one breast into the first water tank 4. The position of the object 2 may be checked by the optical camera 23 such that a position of the breast serving as the object 2 is adjusted to a center of the first water tank 4 serving as a center of an imaging field.

(S505)

The water adjustment unit 5 starts to supply water to the watertight space and to the first water tank 4 of the measurement unit 200. Since the warm water in the watertight space may leak and decrease with operation of the ring array 3, the water adjustment unit 5 continuously supplies a small quantity of water to the watertight space until the measurement is finished. Water supply to the first water tank 4 continues until the first water tank 4 is full of water.

(S506)

The control unit 6 determines whether the first water tank 4 is full of water. If the water is full, the processing proceeds to S507; if the water is not full, the processing returns to S505.

For example, the ring array 3 is used for detection of a water level in the first water tank 4. An example of a water level detection method using the ring array 3 will be described. During the water supply to the first water tank 4, the ring array 3 repeats transmission and reception of the ultrasonic wave at an uppermost portion of the first water tank 4. Since a signal intensity received by the ring array 3 changes according to the water level of the first water tank 4, whether the water is full can be determined by a received signal. That is, the ring array 3 that moves to the uppermost portion of the first water tank 4 and the signal processing unit 7 serve as water level detection units that detect a water level of the medium in the first water tank 4.

The detection of the water level in the first water tank 4 is not limited to the method using the ring array 3. For example, a piezoelectric element may be separately provided at the lower portion of the first water tank 4 to detect the water level by measuring reflection of an ultrasonic wave at a water level surface of the first water tank 4. Alternatively, a laser range finder may be separately provided at the lower portion of the first water tank 4 to detect the water level by measuring a distance from the laser range finder to a buoy floating on a water surface or the like. Further, a full-water state may be determined by output from a water leakage sensor that is separately provided at an upper portion of the outer surface of the first water tank 4. The above-described piezoelectric element, laser range finder and water leakage sensor also serve as a part of the water level detection unit.

In addition, in order to shorten time, warm water with a quantity corresponding to a size of the object 2 may be supplied to the first water tank 4 in advance before S504. The size of the object 2, that is, a volume thereof is calculated by the signal processing unit 7 based on a chest circumference information of the subject 1 input from the input/output unit 9, or a 3D image obtained by using the optical camera 23 or the ring array 3. Warm water having a difference volume between a volume of the first water tank 4 and the calculated volume of the object 2 is supplied to the first water tank 4 in advance. A medium supply to the first water tank 4 is performed by controlling the pump 31 by the control unit 6 based on monitoring of a supply quantity using a flow meter or the like. That is, the signal processing unit 7 serves as a volume calculation unit that calculates the volume of the object. Further, the control unit 6 functions as a medium supply unit that supplies a medium, which has a quantity calculated based on a volume calculated by the volume calculation unit, to the first water tank 4.

(S507)

The water adjustment unit 5 stops supplying water to the first water tank 4 and notifies the control unit 6 that an ultrasonic measurement of the object 2 can be started. That is, the ultrasonic measurement of the object 2 can be started in a state where the first water tank 4 is full of water.

(S508)

The ring array 3 repeats the movement in the vertical direction and the transmission and reception of the ultrasonic wave based on a control signal from the controller for the measurement unit 200. When it is detected or estimated that the ring array 3 has reached a lowermost portion of the first water tank 4 or the object 2 has deviated from the imaging field, imaging is automatically completed, and the ring array 3 returns to the uppermost portion of the first water tank 4 that serves as an imaging start position. The signal obtained at the ring array 3 is subjected to image processing calculation using the signal processing unit 7, and the tomographic images of the object 2 are generated at each position in the vertical direction. The generated tomographic images are displayed on the monitor of the input/output unit 9.
(S509)

If the measurement is completed, the processing proceeds to S510. Further, in a case where the same subject 1 is continuously measured, for example, in a case where the other breast is measured or where re-measurement is necessary, the processing returns to S508.
(S510)

The water adjustment unit 5 starts to drain water from the first water tank 4. During water drainage, a user wipes residual water on the body surface of the subject 1 and performs alcohol disinfection and cleans the first water tank 4 or the cushion member 16.
(S511)

The water adjustment unit 5 stops supplying water to the watertight space. After the water supply to the watertight space is stopped, the measurement is completed, and the processing proceeds to FIG. 5(c).
(S512)

Water drainage from the reserve water tank 34 is performed by the operation of the plug 38, or the control of the plug 38 performed by the controller for the water adjustment unit 5 based on an instruction of the user. If necessary, an inner side of the second water tank 10 may be dried by the hairdryer 22.

With the above processing flow, the tomographic images of the object 2 can be generated by the ultrasonic CT device 100 that can reduce an influence of a medium overflowing from the water tank on a periphery of the water tank. Further, since the object 2 is subjected to the ultrasonic measurement in a state where the first water tank 4 is full of water, tomographic images at a position where the ring array 3 is sufficiently close to the body surface of the subject 1 can be generated. That is, breakdown of the ultrasonic CT device cannot be caused and a wide imaging field in the vertical direction can be ensured.

Second Embodiment

Figure 6A:
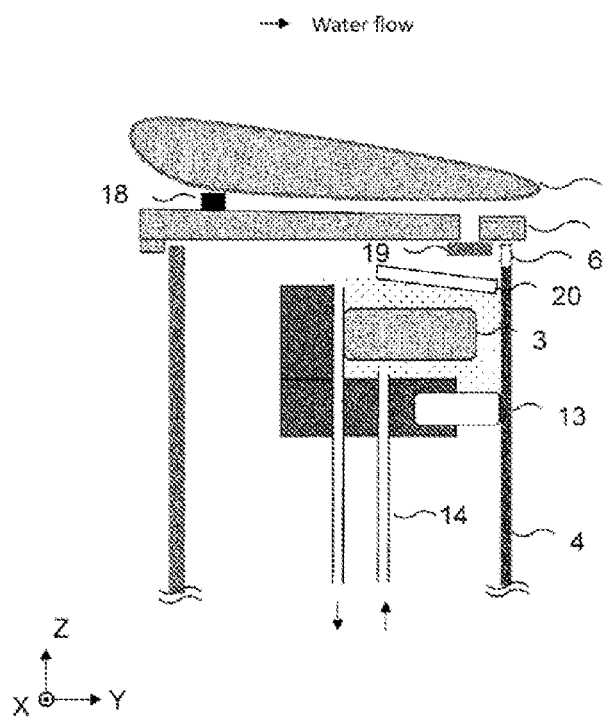
FIGS. 6(a) and 6(b) illustrate views showing a structure of the measurement unit 200 according to a second embodiment.
Figure 6B:
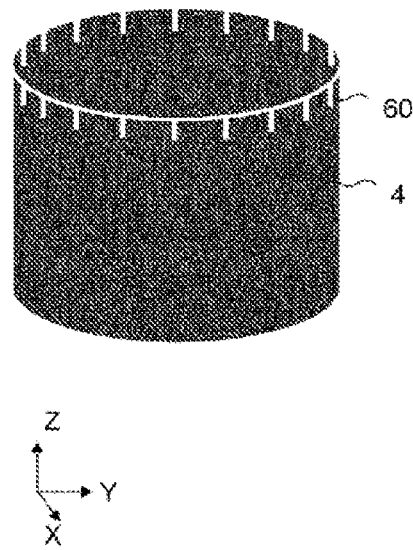

An embodiment improving a water drainage capacity will be described with reference to FIG. 6. FIG. 6(a) is a cross-sectional view of the measurement unit 200 according to this embodiment, and FIG. 6(b) is a perspective view of the first water tank 4 according to this embodiment. Further, an entire configuration and a processing flow according to this embodiment are the same as those in the first embodiment, so descriptions thereof will be omitted. A structure of the first water tank 4 which is different from that of the first embodiment will be described.

Slits 60 are provided in a wall surface of an uppermost portion of the first water tank 4 according to this embodiment. It is desired that the slits 60 have sizes allowing the medium to pass through and are provided at positions that are difficult to influence transmission and reception of an ultrasonic wave of the ring array 3. For example, in a case where the ring array 3 has a configuration in which eight small portions are combined as shown in FIG. 1(b), it is desired that the slits 60 are disposed at gaps between the small portions. In this case, a width of the slits 60, that is, a circumferential length of the first water tank 4, is equal to or less than the gap between the small portions. Further, a height of the slits 60, that is, a length thereof in a vertical direction is set such that when the ring array 3 moves to the uppermost portion of the first water tank 4, an ultrasonic wave irradiated from the ring array 3 and an ultrasonic wave reflected from the object 2 do not intersect with the slits 60.

Since the slits 60 are provided in the uppermost portion of the first water tank 4, the medium, which overflows from the first water tank 4 due to body movement of the object 2, can be drained through the holes 17, the notches 17a of the lid 15 as well as the slits 60, and thus the water drainage capacity can be improved. Further, in a case where the water drainage capacity is sufficient due to the slits 60 provided at the first water tank 4, the holes 17 and the notches 17a may not be provided in the lid 15.

Third Embodiment

An embodiment in which mixing of a medium overflowing from the first water tank 4 and a medium of the watertight space is prevented will be described with reference to FIG. 7. FIG. 7 is a cross-sectional view of the measurement unit 200 according to this embodiment. It is desired that the medium of the watertight space is separated from a contamination-prone medium overflowing from the first water tank 4 and without being mixed with the same, the watertight space being around the ring array 3 and having a lot of micro-components difficult to clean. Usability of an ultrasonic CT device is improved from a maintenance point of view by separating the medium of the watertight space from the medium overflowing from the first water tank 4. Further, an entire configuration and a processing flow according to this embodiment are the same as those of the first embodiment, so descriptions thereof is omitted. A structure of the lid 15 which is different from that of the first embodiment will be described.

The tube 14 is connected to the holes 17 of the lid 15 according to this embodiment. The tube 14 connected to the holes 17 may be disposed such that the medium is drained to a lower portion of the second water tank 10, and may be directly connected to the water adjustment unit 5.

The tube 14 is connected to the holes 17 of the lid 15, so that mixing of the medium overflowing from the first water tank 4 and the medium of the watertight space can be prevented. In a case where the tube 14 connected to the holes 17 is directly connected to the water adjustment unit 5, the water drainage can be supported by making a negative pressure inside the tube 14 with the pump 31.

Fourth Embodiment

Figure 8A:
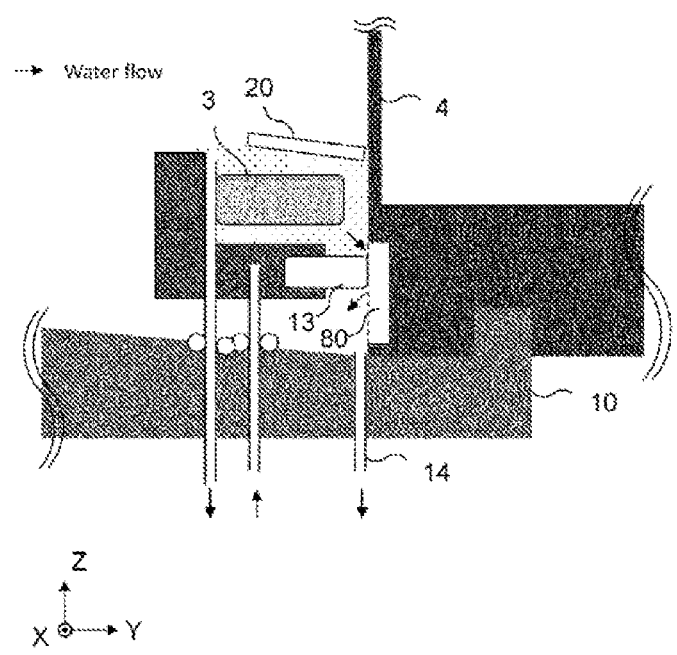
FIGS. 8(a) and 8(b) illustrate views showing a structure of the measurement unit 200 according to a fourth embodiment.
Figure 8B:
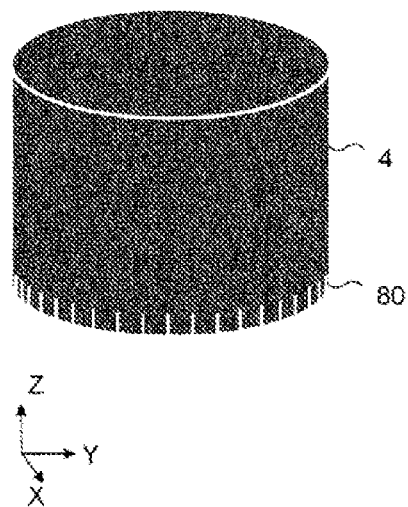

An embodiment in which water drainage of a medium of the watertight space is facilitated will be described with reference to FIG. 8. FIG. 8(a) is a cross-sectional view of the measurement unit 200 according to this embodiment, and FIG. 8(b) is a perspective view of the first water tank 4 according to this embodiment. Further, an entire configuration and a processing flow according to this embodiment are the same as those of the first embodiment, so descriptions thereof will be omitted. A structure of the first water tank 4 which is different from that of the first embodiment will be described.

Grooves 80 are provided in an outer surface of a lowermost portion of the first water tank 4 according to this embodiment. The grooves 80 are not in connection with an inner wall of the first water tank 4 and have a size allowing the medium to pass through. A height of the grooves 80, that is, a length in a vertical direction, is equal to or larger than a height of the rubber member 13. Further, a depth of the grooves 80, that is, a length of the first water tank 4 in a radial direction, does not allow the rubber member 13 to contact a bottom of the grooves 80.

Since the grooves 80 are provided in an outer surface of the lowermost portion of the first water tank 4, when the ring array 3 is moved to the lowermost portion of the first water tank 4, the medium of the watertight space can be drained easily.

The invention is described based on the above four embodiments. However, the ultrasonic CT device of the invention is not limited to the above embodiments, and constituent elements can be modified and embodied within the scope not deviated from the spirit of the invention. The plurality of constituent elements disclosed in the above embodiments may be appropriately combined. Further, some of the constituent elements described in the above embodiments may be omitted.

REFERENCE SIGN LIST 1 subject
2 object
3 ring array
4 first water tank
5 water adjustment unit
6 control unit
7 signal processing unit
8 storage unit
9 input/output unit
10 second water tank
11 ball screw shaft
12 motor
13 rubber member
14 tube
15 lid
16 cushion member
17 hole
17a notch
18 holding member
19 thin filter
20 cover
21 ultrasonic control signal wire
22 hairdryer
23 optical camera
24 transparent member
31 pump
32 filter
33 sterilization device
34 reserve water tank
35 heater
36 fan
37 degassing device
38 plug
60 slit
80 groove
100 ultrasonic CT device
110 bed
120 console
200 measurement unit

The invention claimed is:

1. An ultrasonic CT device comprising:
a first water tank configured such that an object is inserted therein, the first water tank being filled with a medium through which an ultrasonic wave passes;
an ultrasonic element array arranged adjacent to and spaced apart from an outer surface of the first water tank, the ultrasonic element array being configured to irradiate the object with an ultrasonic wave, and to detect an ultrasonic wave reflected by the object; and
a central processing unit configured to execute instruction stored in a memory to generate a tomographic image of the object based on a signal obtained by the ultrasonic element array,
the ultrasonic CT device further comprising:
a second water tank configured to house the first water tank and the ultrasonic element array, wherein the ultrasonic element array is housed between the outer surface of the first water tank and an inner surface of the second water tank; and
a lid disposed at an upper portion of the second water tank, extending at least from the outer surface of the first water tank to the inner surface of the second water tank, and in contact with the outer surface of the first water tank and the inner surface of the second water tank, the lid having a hole or a notch adjacent to the first water tank, the hole or notch leading into the second water tank and is configured to drain the medium.

2. The ultrasonic CT device according to claim 1, wherein the central processing unit is further configured to:
detect a water level of the medium in the first water tank; and
control a quantity of the medium in the first water tank based on the detected water level.

3. An ultrasonic CT device comprising:
a first water tank configured such that an object is inserted therein, the first water tank being filled with a medium through which an ultrasonic wave passes;
an ultrasonic element array arranged on an outer surface of the first water tank, the ultrasonic element array being configured to irradiate the object with an ultrasonic wave, and to detect an ultrasonic wave reflected by the object; and
a central processing unit configured to execute instruction stored in a memory to generate a tomographic image of the object based on a signal obtained by the ultrasonic element array and calculate a volume of the object in the first water tank,
the ultrasonic CT device further comprising:
a second water tank configured to house the first water tank and the ultrasonic element array;
a lid disposed at an upper portion of the second water tank, the lid having a hole or a notch opening into the second water tank adjacent to the first water tank, the hole or notch is configured to drain the medium; and
a medium supply unit configured to supply a medium, which has a quantity calculated based on the calculated volume, to the first water tank.

4. The ultrasonic CT device according to claim 3, further comprising:
an optical camera configured to image the object, wherein the central processing unit is further configured to calculate the volume of the object based on an image obtained by the optical camera.

5. The ultrasonic CT device according to claim 3, wherein the central processing unit is further configured to calculate the volume of the object based on a signal obtained by the ultrasonic element array.

6. The ultrasonic CT device according to claim 1, further comprising:
   a cushion member that is provided on the lid; and
   a rubber member that is provided between the lid and the cushion member, and is configured to maintain a path for the medium to the hole or the notch.

7. The ultrasonic CT device according to claim 1, wherein the lid is inclined toward the first water tank.

8. The ultrasonic CT device according to claim 1, further comprising:
   a blower configured to blow warm air into the second water tank.

9. The ultrasonic CT device according to claim 1, wherein a slit is provided in an uppermost portion of the first water tank.

10. The ultrasonic CT device according to claim 9, wherein the slit is provided in a gap in the ultrasonic element array.

11. The ultrasonic CT device according to claim 1, further comprising:
    a tube configured to connect the hole or the notch to a lower portion of the second water tank.

12. The ultrasonic CT device according to claim 1, wherein a groove is provided in an outer surface of a lowermost portion of the first water tank.

13. An ultrasonic CT device, comprising:
    a first water tank configured such that an object is inserted therein, the first water tank being filled with a medium through which an ultrasonic wave passes;
    an ultrasonic element array arranged adjacent to and spaced apart from an outer surface of the first water tank, the ultrasonic element array being configured to irradiate the object with an ultrasonic wave, and to detect an ultrasonic wave reflected by the object; and
    a central processing unit configured to execute instruction stored in a memory to generate a tomographic image of the object based on a signal obtained by the ultrasonic element array,
    the ultrasonic CT device further comprising:
       a second water tank configured to house the first water tank and the ultrasonic element array, wherein the ultrasonic element array is housed between the outer surface of the first water tank and an inner surface of the second water tank; and
       a lid provided at an upper portion of the second water tank and extending at least from the outer surface of the first water tank to the inner surface of the second water tank,
    wherein a slit is provided in an uppermost portion of the first water tank.

* * * * *